(12) United States Patent
Burdock

(10) Patent No.: US 9,889,172 B2
(45) Date of Patent: Feb. 13, 2018

(54) THERAPEUTIC PATCH

(71) Applicant: Nicole Burdock, Oakland, CA (US)

(72) Inventor: Nicole Burdock, Oakland, CA (US)

(73) Assignee: Nicole Burdock, Oakland, CA (US)

( * ) Notice: Subject to any disclaimer, the term of this patent is extended or adjusted under 35 U.S.C. 154(b) by 0 days.

(21) Appl. No.: 14/816,032

(22) Filed: Aug. 2, 2015

(65) Prior Publication Data

US 2017/0028008 A1    Feb. 2, 2017

(51) Int. Cl.
| | | |
|---|---|---|
| *A61K 36/59* | (2006.01) | |
| *A61K 9/70* | (2006.01) | |
| *A61K 36/81* | (2006.01) | |
| *A61K 47/32* | (2006.01) | |
| *A61K 33/42* | (2006.01) | |
| *A61K 36/42* | (2006.01) | |
| *A61K 36/71* | (2006.01) | |
| *A61K 36/56* | (2006.01) | |
| *A61K 36/28* | (2006.01) | |
| *A61M 35/00* | (2006.01) | |
| *A61M 37/00* | (2006.01) | |

(52) U.S. Cl.
CPC ............ *A61K 36/59* (2013.01); *A61K 9/7038* (2013.01); *A61K 9/7061* (2013.01); *A61K 33/42* (2013.01); *A61K 36/28* (2013.01); *A61K 36/42* (2013.01); *A61K 36/56* (2013.01); *A61K 36/71* (2013.01); *A61K 36/81* (2013.01); *A61K 47/32* (2013.01); *A61M 35/00* (2013.01); *A61M 37/00* (2013.01)

(58) Field of Classification Search
None
See application file for complete search history.

(56) References Cited

U.S. PATENT DOCUMENTS

| | | | |
|---|---|---|---|
| 6,830,758 B2 | 12/2004 | Nichols et al. | |
| 2006/0121102 A1* | 6/2006 | Chiang | A61K 9/7061 424/449 |
| 2008/0003273 A1* | 1/2008 | Feldkamp | A61K 9/0014 424/448 |
| 2012/0220962 A1* | 8/2012 | Hsu | A61K 9/0014 604/307 |

* cited by examiner

*Primary Examiner* — Brian Gulledge
(74) *Attorney, Agent, or Firm* — Kali-Law Group, P.C.

(57) ABSTRACT

Therapeutic patches are presented including: a non-permeable sealing layer; a pressure sensitive adhesive layer bonded along the non-permeable sealing layer, where the pressure sensitive adhesive layer includes a formulation of a pressure sensitive adhesive and a heat sensitive homeopathic formulation, where the pressure sensitive adhesive layer is processed at a temperature less than approximately 1000 F; and a releasable layer attached along the pressure sensitive adhesive layer. In some embodiments, the therapeutic patch detectably reduces nausea associated symptoms and menstrual cramping. In some embodiments, the pressure sensitive adhesive layer includes at least approximately 15% by weight of the heat sensitive homeopathic formulation. In some embodiments, the pressure sensitive adhesive layer includes at least approximately 5 to 20% by weight of the heat sensitive homeopathic formulation.

19 Claims, 5 Drawing Sheets

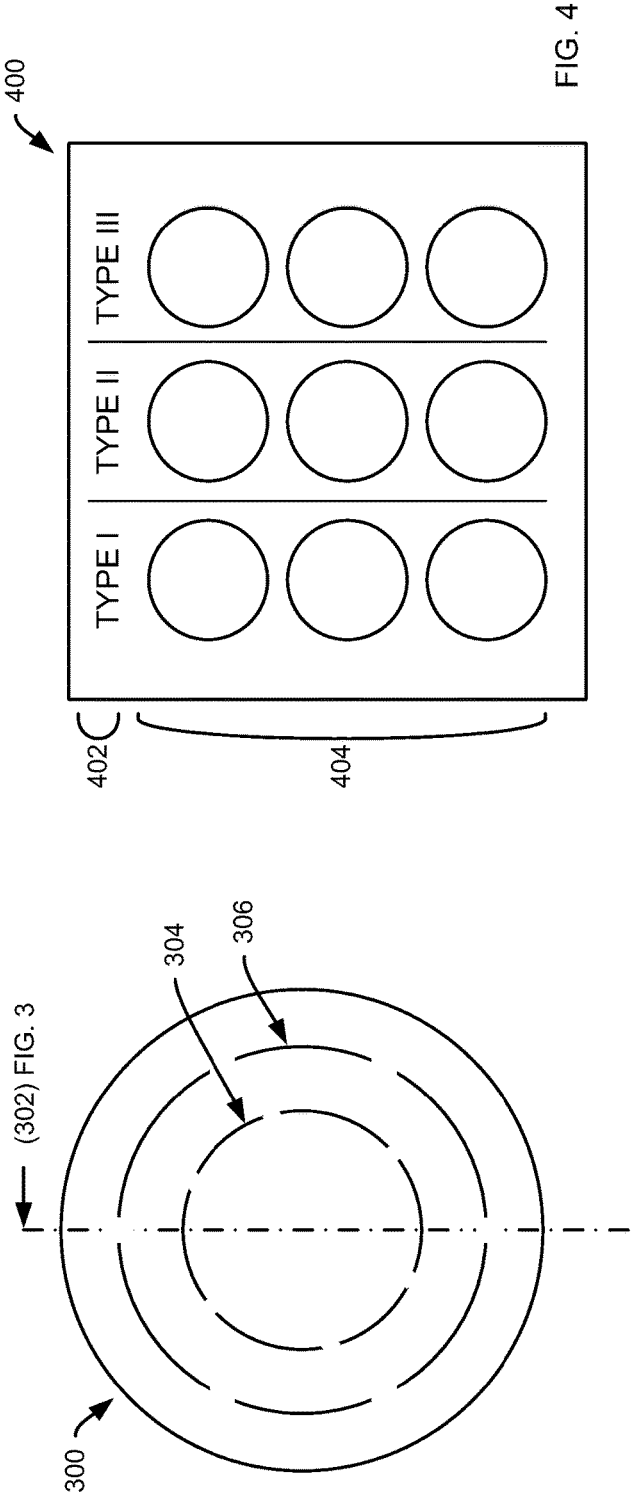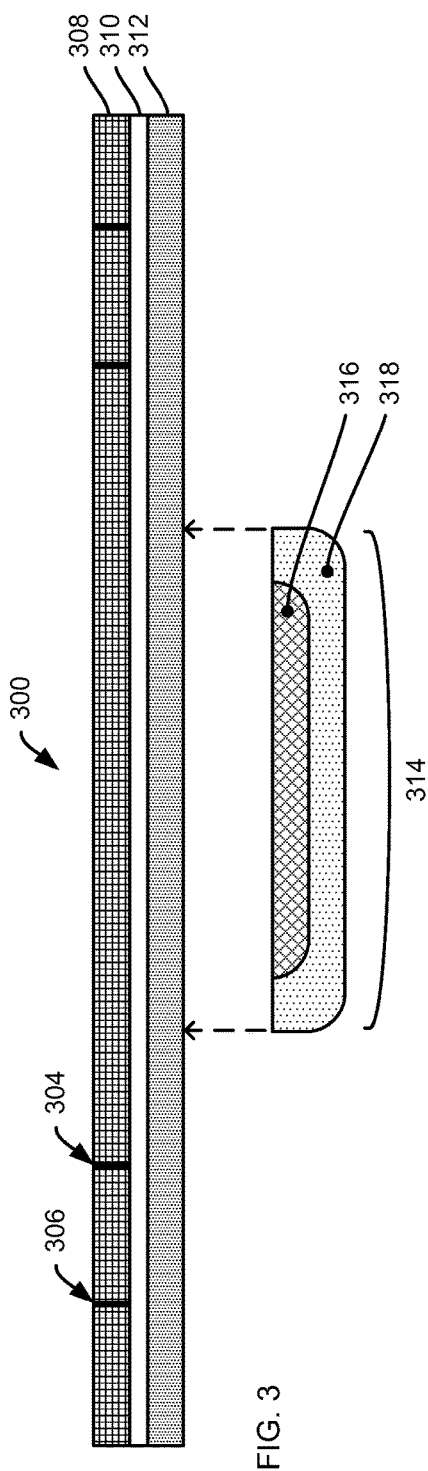

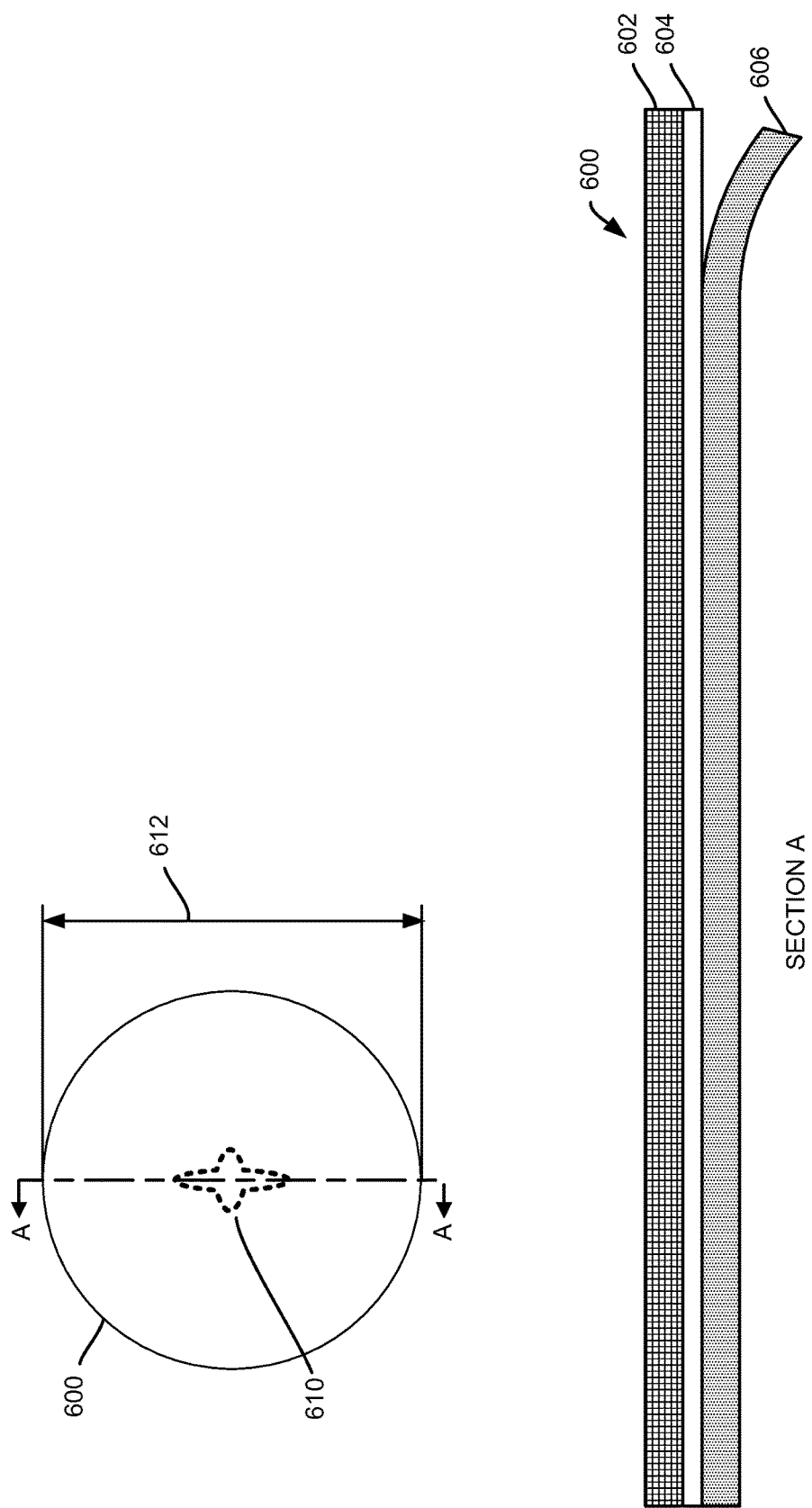

THERAPEUTIC PATCH

BACKGROUND

Nausea associated symptoms can severely disrupt daily normal activity. In modern societies, a hectic lifestyle is common. Dealing with a disruption in that lifestyle may lower quality of life and may induce many other ailments such as for example, anxiety and stress. In addition, nausea associated symptoms may occur with or without the urge to vomit. In cases where the urge to vomit is induced, patients may not feel hungry and may further suffer from lack of sufficient nutrition. Because nausea can be unpredictable and sudden, carrying appropriate medications may not always be convenient. Furthermore, some medications may adversely affect concentration or impair the ability to operate machinery which may exacerbate the problem. In recent years, conventional medicine has turned to alternative means to accomplish effective treatments. Herbal formulations, acupressure, acupuncture, and chiropractics are a few alternative solutions that conventional medicine has begun, not only to recognize, but advocate as well. As such, therapeutic patches are presented herein.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

As such, therapeutic patches are presented including: a non-permeable sealing layer; a pressure sensitive adhesive layer bonded along the non-permeable sealing layer, where the pressure sensitive adhesive layer includes a formulation of a pressure sensitive adhesive and a heat sensitive homeopathic formulation, where the pressure sensitive adhesive layer is processed at a temperature less than approximately 100° F.; and a releasable layer attached along the pressure sensitive adhesive layer. In some embodiments, the therapeutic patch detectably reduces nausea associated symptoms and menstrual cramping. In some embodiments, the pressure sensitive adhesive layer includes at least approximately 15% by weight of the heat sensitive homeopathic formulation. In some embodiments, the pressure sensitive adhesive layer includes at least approximately 5 to 20% by weight of the heat sensitive homeopathic formulation. In some embodiments, the pressure sensitive adhesive layer includes at least approximately 2 to 30% by weight of the heat sensitive homeopathic formulation. In some embodiments, the heat sensitive homeopathic formulation includes: a solvent; and a number of active ingredients selected for reducing nausea associated symptoms and menstrual cramping. In some embodiments, the number of active ingredients selected for reducing nausea associated symptoms and menstrual cramps are selected from the group consisting of: *belladonna*, magnesia phosphorica, colcynthis, *pulsatilla*, nux vomica, *cocculus indicus, tabacum*, sepia, *chamomilla*, and calendula. In some embodiments, the solvent includes approximately a 20% ethanol solution. In some embodiments, the *belladonna* is present up to about 30% by weight of the number of active ingredients; magnesia phosphorica is present up to about 30% by weight of the number of active ingredients; colocynthis is present up to about 30% by weight of the number of active ingredients; *pulsatilla* is present up to about 10% by weight of the number of active ingredients; nux vomica is present up to about 10% by weight of the number of active ingredients; *chamomilla* is present up to about 5% by weight of the number of active ingredients; and calendula is present up to about 5% by weight of the number of active ingredients. In some embodiments, where the *cocculus indicus* is present up to about 20% by weight of the number of active ingredients; nux vomica is present up to about 40% by weight of the number of active ingredients; *tabacum* is present up to about 15% by weight of the number of active ingredients; sepia is present up to about 15% by weight of the number of active ingredients; *chamomilla* is present up to about 5% by weight of the number of active ingredients; and calendula is present up to about 5% by weight of the number of active ingredients. In some embodiments, the pressure sensitive adhesive is an acrylic copolymer. In some embodiments, the non-permeable sealing layer is a polyethylene foam. In some embodiments, the non-permeable sealing layer is a polyethylene foam is corona treated before bonding the pressure sensitive adhesive layer. In some embodiments, the pressure sensitive adhesive has a peel value of approximately 1.5 pounds per square inch. In some embodiments, the nausea associated symptoms are selected from the group consisting of: motion sickness, chemotherapy induced nausea vomiting (CINV), pregnancy (morning sickness), anxiety induced irritable bowel syndrome, Crohn's Disease, medication induced dizziness, vertigo, stress, migraines, general anxiety, and depression.

In other embodiments, methods for treating nausea associated symptoms are presented including: receiving a therapeutic patch, the therapeutic patch including, a non-permeable sealing layer; a pressure sensitive adhesive layer bonded along the non-permeable sealing layer, where the pressure sensitive adhesive layer includes a formulation of a pressure sensitive adhesive and a heat sensitive homeopathic formulation, where the pressure sensitive adhesive layer is processed at a temperature less than approximately 100° F., and a releasable layer attached along the pressure sensitive adhesive layer; and applying the therapeutic patch to seal a navel cavity area. In some embodiments, methods further include removing the therapeutic patch when the nausea causing activity terminates. In some embodiments, methods further include removing the therapeutic patch after less than approximately 12 hours. In some embodiments, methods further include selecting the therapeutic patch based on a criteria selected from the group consisting of: a formulation, a patient characteristic formulation, a condition formulation and any combination thereof.

BRIEF DESCRIPTION OF THE DRAWINGS

The present invention is illustrated by way of example, and not by way of limitation, in the figures of the accompanying drawings and in which like reference numerals refer to similar elements and in which:

FIG. 3 is an illustrative representation of a therapeutic patch in cross-section in accordance with embodiments of the present invention;

FIG. 4 is an illustrative representation of a package of therapeutic patches in accordance with embodiments of the present invention;

FIG. 6 is an illustrative representation of a therapeutic patch in use in accordance with embodiments of the present invention.

DETAILED DESCRIPTION

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

Figure 1:
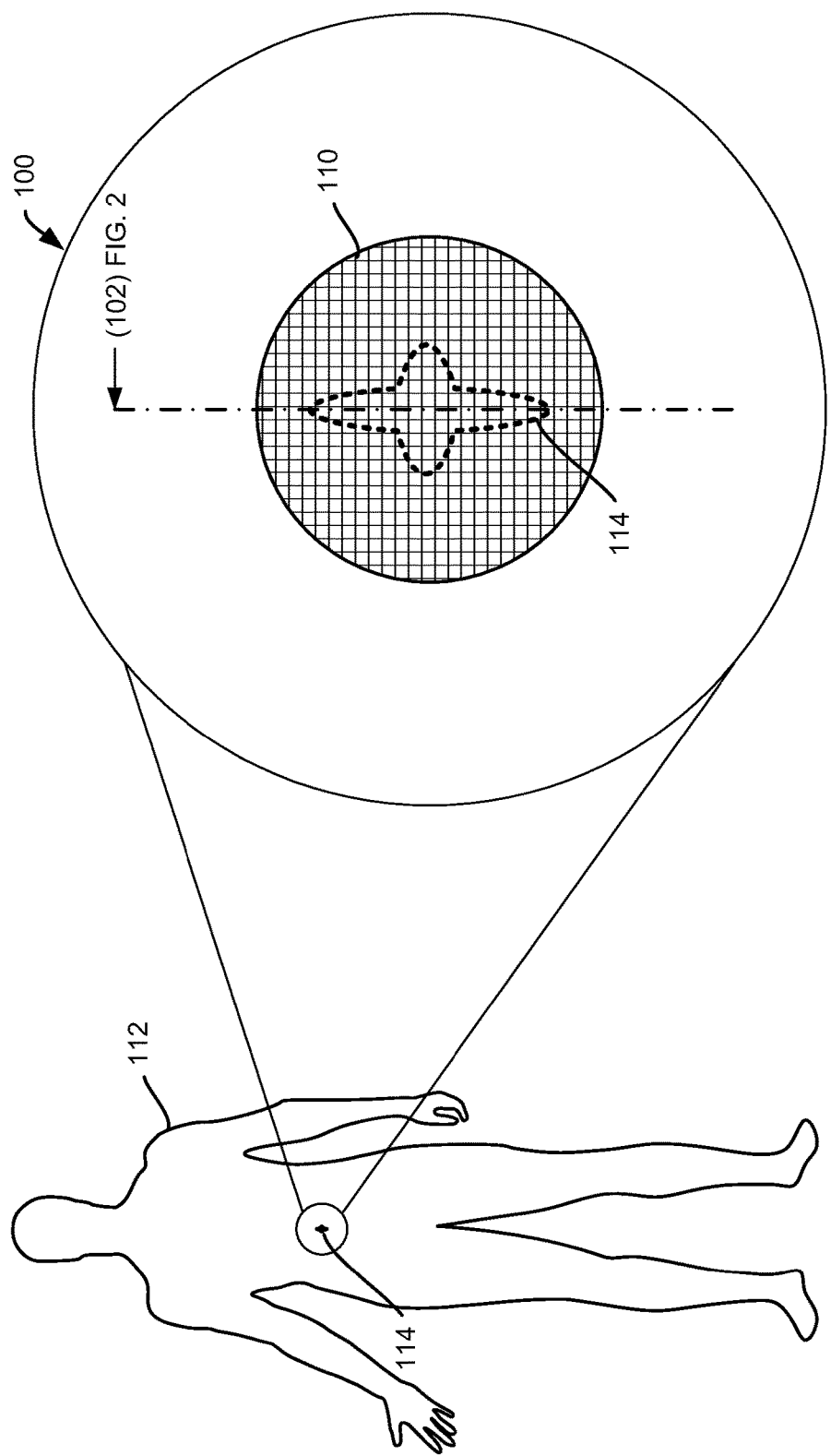
FIG. 1 is an illustrative representation of a therapeutic patch in use in accordance with embodiments of the present invention.

FIG. 1 is an illustrative representation of a therapeutic patch 110 in use in accordance with embodiments of the present invention. In particular, FIG. 1 represents use of a therapeutic patch 110 utilized on an adult male human 112 although use of therapeutic patches are not so limited and may be utilized on children and adults both male and female without limitation in embodiments provided herein. As illustrated, exploded view 100 illustrates placement of therapeutic patch 110 over navel cavity 114. It may be noted that therapeutic patch 110 completely covers and seals naval cavity 114. Centerline 102 indicates a cross-sectional view that will be discussed in further detail below for FIG. 2. FIG. 1 is provided to clarify the context and operative position of therapeutic patch embodiments described herein. As contemplated herein, therapeutic patches may be utilized to demonstrably reduce or eliminate nausea associated conditions such as, for example, motion sickness, chemotherapy induced nausea and vomiting (CINV), pregnancy (morning sickness), anxiety induced irritable bowel syndrome, irritable bowel syndrome, Crohn's Disease, medication induced dizziness, vertigo, stress, and depression. Additionally, therapeutic patches may be utilized to address and support any number of patient conditions such as, for example, infertility, frequent miscarriage, epilepsy, diarrhea, umbilical pain, urine retention, painful urination, rectal prolapse, arthritis, high blood pressure, hemorrhoids, malaise, and menstrual cramps. Therefore, it may be appreciated that embodiments described herein may provide relief for a variety of disease related symptoms.

Figure 2:
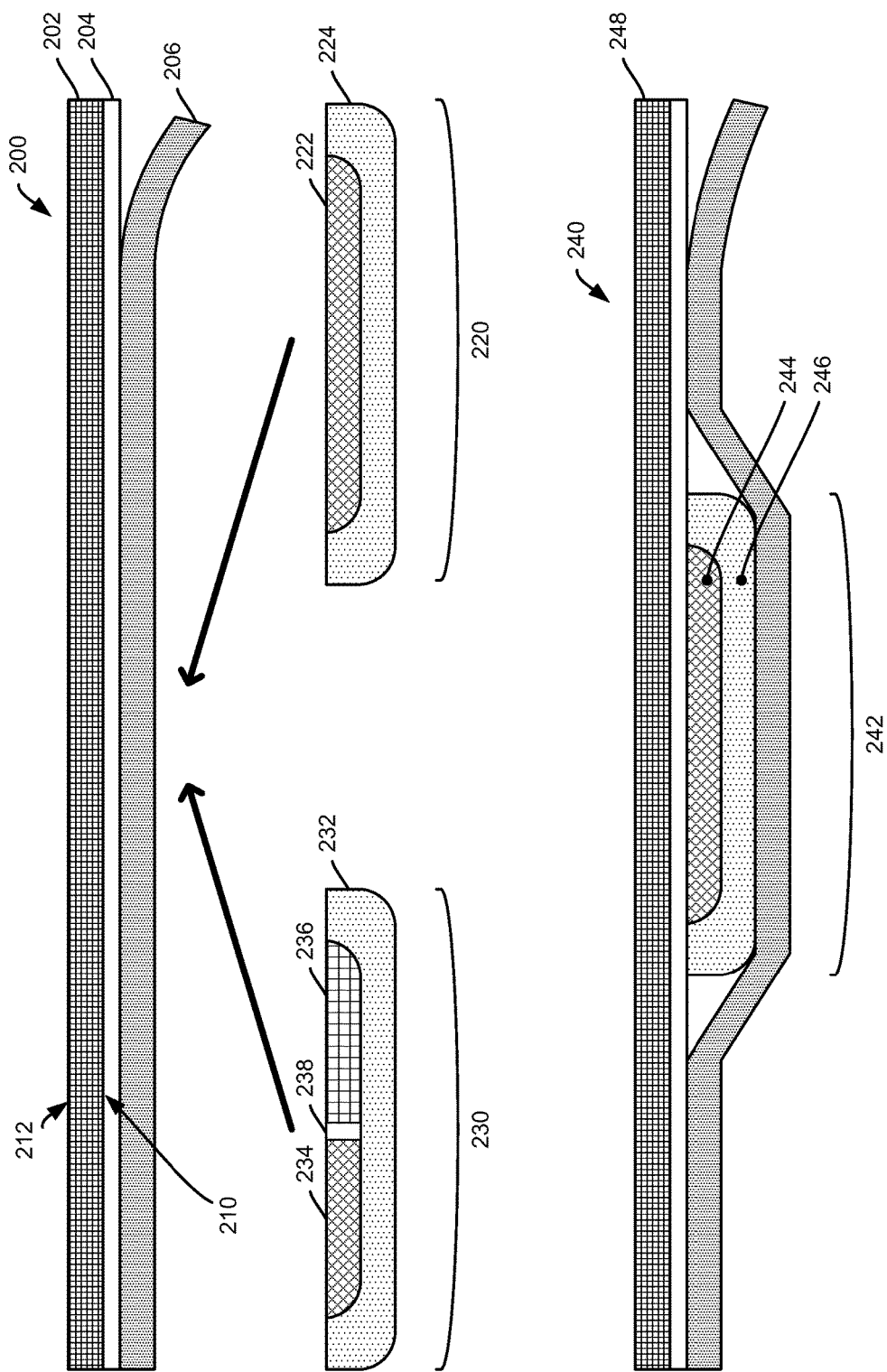
FIG. 2 is an illustrative representation of a therapeutic patch in cross-section in accordance with embodiments of the present invention.

FIG. 2 is an illustrative representation of a therapeutic patch 200 in cross-section in accordance with embodiments of the present invention. As illustrated, therapeutic patch 200 includes several layers, namely, non-permeable sealing layer 202 having an inner surface 210 and an outer surface 212; pressure sensitive adhesive layer 204 attached or bonded along inner surface 210; and releasable layer 206 attached along the pressure sensitive adhesive layer 204. Non-permeable sealing layer embodiments may be manufactured from any non-breathable material that is sufficiently flexible to accommodate movement of a patient without departing from embodiments herein. Thus, in some embodiments, non-permeable layers may be manufactured from a non-breathable polyester, polyethylene, or silicone without limitation. In some embodiments, non-permeable sealing layer embodiments may be manufactured from a non-breathable and non-stretchable material.

In addition, non-permeable sealing layer embodiments may be sized and shaped in any number of configurations as for example, a circle, a triangle, a polygon, or any shape having coverage in a range of approximately 1 to 20 square inches without departing from embodiments provided herein. In some embodiments, non-permeable sealing layers may be printable or may include holograms without limitation. In some embodiments, a permeable flexible layer may be added (not shown) to provide additional area for adhesion and may provide durability advantages. In still other embodiments, non-permeable sealing layers may be waterproof. Further, in embodiments any number of pressure sensitive adhesives (PSA) may be utilized without limitation. For example, a medical grade non-allergenic PSA may be utilized in embodiments. In addition, a high tack PSA may be selected to provide repeated removal and application of therapeutic patch embodiments without limitation. Still further releasable layer embodiments may utilize any releasable material without departing from embodiments provided herein.

Further illustrated in FIG. 2 are medicinals 220 and 230. Medicinal 220 includes formulation 222, which may be sealed to a navel cavity by non-permeable sealing layer 202. Medicinal 220 further includes semi-permeable layer 224 for securing the formulation 222. In some embodiments, therapeutic patches having different formulations may be separately packaged. In this manner, an appropriate medicinal may be selected by a patient or by a caregiver. Packaging embodiments will be discussed in further detail below for FIG. 4. In addition, medicinal 230 includes formulations 234 and 236 may be temporarily separated by burst membrane 238. In some embodiments it may be desirable to temporarily separate at least two formulations that are therapeutically reactive when mixed. In this manner, the therapeutic viability of formulations may be timed to actual use. Medicinal 230 further includes semi-permeable layer 232 for securing the formulations 234 and 236. Formulations may include any number of compounds such as: mugwort, salt, ginger, garlic, ginger processed aconite (fu zi)/aconite cake, pinellia rhizome (ban xia), mint, orange peel, evodia fruit powdered extract (wu zhu yu), fennel, and any combination thereof in accordance with embodiments of the present invention and without limitation. In addition, formulations may include further properties that may provide improved treatment and formulation delivery such as, for example, a heat activation property, a water activation property, and a water solubility property.

Further illustrated in FIG. 2 is therapeutic patch 240 having medicinal 242 incorporated with therapeutic patch 240. As above, Medicinal 242 includes formulation 244, which may be sealed to a navel cavity by non-permeable sealing layer 248. Medicinal 242 further includes semi-permeable layer 246 for securing the formulation 244. In addition, medicinal 242 may include a burst membrane (not shown) and at least two formulations (not shown) such as illustrated by medicinal 230. As above, it may be desirable to temporarily separate at least two formulations that are therapeutically reactive when mixed. In this manner, the therapeutic viability of the formulation may be timed to actual use. Formulations may include any number of compounds such as: mugwort, salt, ginger, garlic, ginger processed aconite (fu zi)/aconite cake, pinellia rhizome (ban xia), mint, orange peel, evodia fruit powdered extract (wu zhu yu), fennel, and any combination thereof in accordance with embodiments of the present invention and without limitation. In addition, formulations may include further properties that may provide improved treatment and formulation delivery such as, for example, a heat activation property, a water activation property, and a water solubility property.

FIG. 3 is an illustrative representation of therapeutic patch 300 in cross-section in accordance with embodiments of the present invention. In particular, centerline 302 indicates a cross-sectional view for perforated embodiments provided herein. As illustrated, therapeutic patch 300 may include a number of perforations 304 and 306 that may provide at least one additionally sized therapeutic patch. Perforations may be sized and spaced in any number of configurations known in the art without departing from embodiments provided herein. As above, therapeutic patch 300 includes several layers, namely, non-permeable sealing layer 308 which may include perforations 304 and 306; pressure sensitive adhesive layer 310; and releasable layer 312 attached along the pressure sensitive adhesive layer 310. Non-permeable sealing layer embodiments may be manufactured from any non-breathable material that is sufficiently flexible to accommodate movement of a patient without departing from embodiments herein. Thus, in some embodiments, non-permeable layers may be manufactured from a non-breathable polyester, polyethylene, or silicone without limitation. In some embodiments, non-permeable sealing layer embodiments may be manufactured from a non-breathable and non-stretchable material.

In addition, non-permeable sealing layer embodiments may be sized and shaped in any number of configurations as for example, a circle, a triangle, a polygon, or any shape having coverage in a range of approximately 1 to 20 square inches without departing from embodiments provided herein. In some embodiments, non-permeable sealing layers may be printable or may include holograms without limitation. In some embodiments, a permeable flexible layer may be added (not shown) to provide additional area for adhesion and may provide durability advantages. In still other embodiments, non-permeable sealing layers may be waterproof. Further, any number of pressure sensitive adhesives (PSA) may be utilized to provide pressure sensitive adhesive layer embodiments. For example, a medical grade non-allergenic PSA may be utilized in embodiments. In addition, a high tack PSA may be selected to provide repeated removal and application of therapeutic patch embodiments without limitation. Still further releasable layer embodiments may utilize any releasable material without departing from embodiments provided herein.

Further illustrated in FIG. 3 is medicinal 314. Medicinal 314 includes formulation 316, which may be sealed to a navel cavity by non-permeable sealing layer 308. Medicinal 314 further includes semi-permeable layer 318 for securing the formulation 316. In some embodiments, therapeutic patches having different formulations may be separately packaged with therapeutic patches. In this manner, an appropriate medicinal may be selected by a patient or by a caregiver. Packaging embodiments will be discussed in further detail below for FIG. 4. Formulations may include any number of compounds such as: mugwort, salt, ginger, garlic, ginger processed aconite (fu zi)/aconite cake, pinellia rhizome (ban xia), mint, orange peel, evodia fruit powdered extract (wu zhu yu), fennel, and any combination thereof in accordance with embodiments of the present invention and without limitation. In addition, formulations may include further properties that may provide improved treatment and formulation delivery such as, for example, a heat activation property, a water activation property, and a water solubility property. As above, medicinals may include a burst wall (not shown) and at least two formulations separated (not shown) by the burst wall.

FIG. 4 is an illustrative representation of package 400 of therapeutic patches 404 in accordance with embodiments of the present invention. As illustrated, package 400 may provide any of a number of different types 402 of therapeutic patches 404. As may be appreciated, packaging therapeutic patches having different formulations may provide flexibility in selecting an appropriate formulation. Therapeutic patches may be grouped by any criterion such as, for example, a formulation, a patient characteristic formulation, and a condition formulation without limitation and without departing from embodiments provided herein. In a patient characteristic formulation, for example, therapeutic patches may be grouped by patient weight such that an appropriate dosage may be achieved for different patients having different weights. It may be appreciated that any number and variety of criteria may be utilized for grouping without departing from embodiments provided herein.

Figure 5:
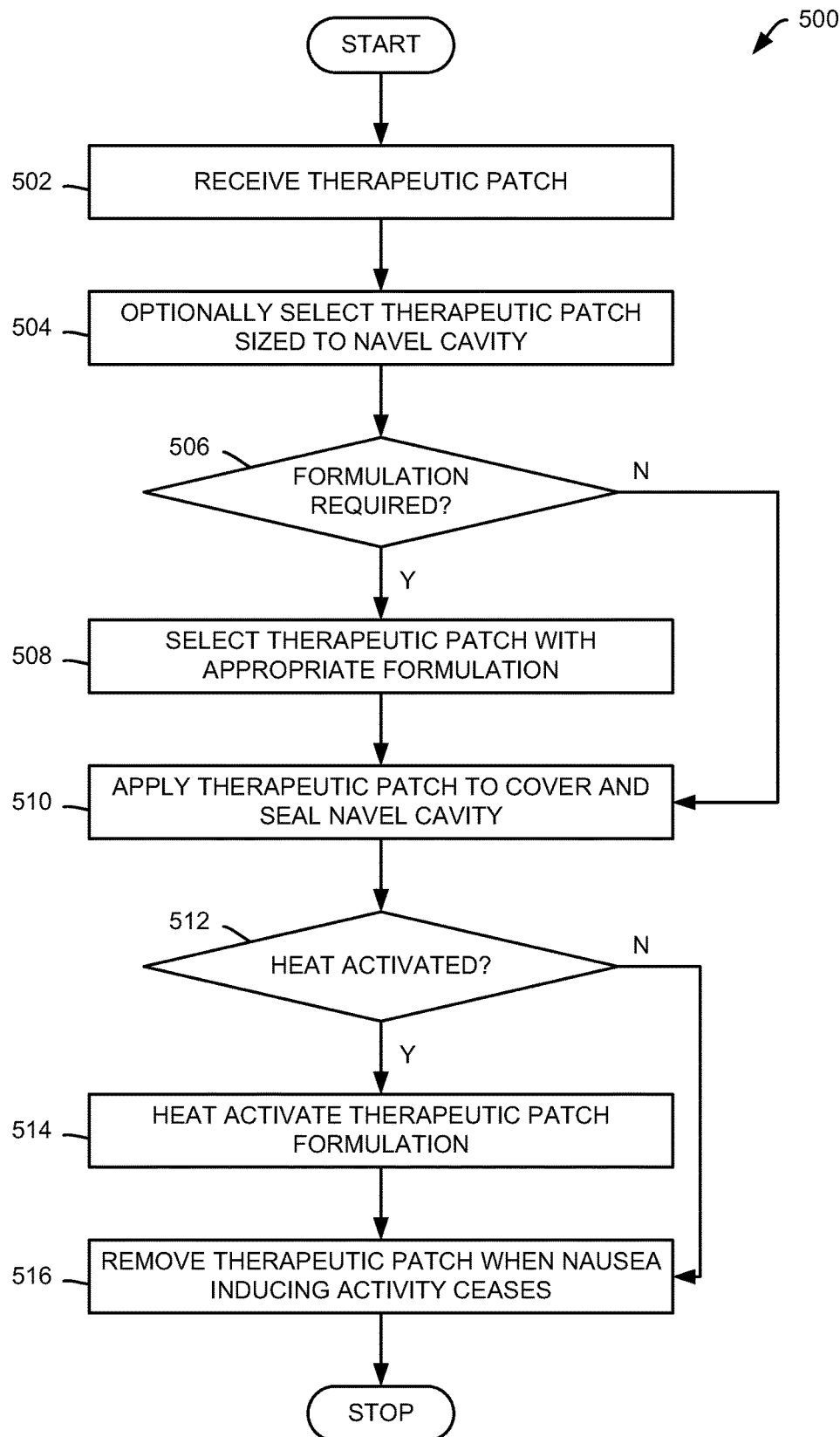
FIG. 5 is an illustrative flowchart of methods for a treatment utilizing a therapeutic patch in accordance with embodiments of the present invention.

FIG. 5 is an illustrative flowchart 500 of methods for a treatment utilizing a therapeutic patch in accordance with embodiments of the present invention. At a first step 502, the method receives a therapeutic patch. As noted above, therapeutic patch embodiments include a non-permeable sealing layer having an inner surface and an outer surface, a pressure sensitive adhesive layer bonded along the inner surface, and a releasable layer attached along the pressure sensitive adhesive layer. At a next step 504, the method continues to optionally select a therapeutic patch sized to a navel cavity. In some embodiments, therapeutic patches may be provided having various sizes. In other embodiments, therapeutic patches may be provided having perforations such that various sizes may be selected from a single uniform size. At a next step 506, the method determines whether a formulation is required. If the method determines at a step 506 that a formulation is required, the method continues to a step 508 to select a therapeutic patch having an appropriate formulation, whereupon the method continues to a step 510. In some embodiments, medicinals may be separately packaged or integrated with therapeutic patches as noted above. If the method determines at a step 508 that a formulation is not required, the method continues to a step 510 to apply a therapeutic patch to cover and seal the navel cavity.

At a next step 512, the method determines whether heat activation is required. If the method determines at a step 512 that heat activation is required, the method continues to a step 514 to heat activate the formulation, whereupon the method continues to a step 516. Heat activation may be achieved in any number of manners without departing from embodiments provided herein such as for example, creating frictional heat by vigorously rubbing the therapeutic patch, or by contacting the formulation with a heat source such as heated air or heated water. If the method determines at a step 512 that heat activation is not required, the method continues to a step 516 to remove the therapeutic patch when the nausea inducing activity ceases, whereupon the method ends.

FIG. 6 is an illustrative representation of a therapeutic patch 600 in use in accordance with embodiments of the present invention. As illustrated, therapeutic patch 600 may be place over navel cavity 610. It may be noted that therapeutic patch 600, in some embodiments, completely covers and seals naval cavity 610. However, embodiments need not be limited to covering and sealing the naval cavity. In other embodiments, therapeutic patches may be applied along other parts of the body without limitation. Centerline A indicates a cross-sectional view that will be discussed in further detail. Therapeutic patch embodiments may be circular having a diameter 612 that may range from approximately 0.5 to 4.0 inches. Although a circular patch is illustrated, any shape may be utilized without departing from embodiments disclosed herein. In some embodiments, selection of a particular size of patch may dictate the amount of formulation deliverable to a patient. As such, a smaller diameter therapeutic patch may deliver a smaller amount of formulation over time as compared with a comparable formulation on a larger diameter therapeutic patch. In embodiments, therapeutic patches may detectably reduce nausea associated symptoms and menstrual cramping. In some embodiments nausea associated symptoms include motion sickness, chemotherapy induced nausea vomiting (CINV), pregnancy (morning sickness), anxiety induced irritable bowel syndrome, Crohn's Disease, medication induced dizziness, vertigo, stress, migraines, general anxiety, and depression.

Referring to section A, a cross-sectional view of therapeutic patch 600 is illustrated. As illustrated, therapeutic patch 600 includes several layers, namely, non-permeable sealing layer 602; pressure sensitive adhesive layer 604 attached or bonded along non-permeable sealing layer 602 and releasable layer 606. Non-permeable sealing layer embodiments may be manufactured from any non-breathable material that is sufficiently flexible to accommodate movement of a patient without departing from embodiments herein. Thus, in some embodiments, non-permeable layers may be manufactured from a non-breathable polyester, polyethylene, or silicone without limitation. In some embodiments, non-permeable sealing layer embodiments may be manufactured from a non-breathable and non-stretchable material. In embodiments, non-permeable sealing layer may be a polyethylene foam that may be corona treated before bonding with pressure sensitive adhesive layers.

In embodiments, PSA layers may include a formulation of a PSA and a heat sensitive homeopathic formulation. Thus, the PSA layer serves at least a dual function of providing tack for therapeutic patch embodiments as well as providing a delivery method for formulations. Importantly, in utilizing homeopathic compounds for use in formulations, care must be taken during manufacturing to prevent destroying the efficacy of the formulations. As such, in embodiments, the PSA later may be processed at temperatures less than approximately 100° F. during manufacture. In embodiments, any number of PSAs may be utilized without limitation. For example, a medical grade non-allergenic PSA may be utilized in embodiments. In some embodiments, the PSA may be an acrylic copolymer. In addition, a high tack PSA may be selected to provide repeated removal and application of therapeutic patch embodiments without limitation. For example, in some embodiments, a PSA having a peel value of approximately 1.5 pounds per square inch may be utilized. Still further releasable layer embodiments may utilize any releasable material without departing from embodiments provided herein. In some embodiments, the PSA layer is preferably at least approximately 15% by weight of the heat sensitive homeopathic formulation. In other embodiments, the PSA layer is preferably approximately 5 to 20% by weight of the heat sensitive homeopathic formulation. In still other embodiments, the PSA layer is preferably approximately 2 to 30% by weight of the heat sensitive homeopathic formulation.

In embodiments, homeopathic formulations may include a solvent and a number of active ingredients selected for reducing nausea associated symptoms and menstrual cramping. In embodiments, a 20% ethanol solvent may be utilized. The following examples are provided for clarity in disclosing formulation embodiments:

Example 1

| Component | Weight % |
|---|---|
| *Belladonna* | up to ~30% |
| *Magnesia Phosphorica* | up to ~30% |
| *Colocynthis* | up to ~20% |
| *Pulsatilla* | up to ~10% |
| *Nux Vomica* | up to ~10% |
| *Chamomilla* | up to ~5% |
| *Calendula* | up to ~5% |

Example 2

| Component | Weight % |
|---|---|
| *Cocculus Indicus* | up to ~40% |
| *Nux Vomica* | up to ~30% |
| *Tabacum* | up to ~15% |
| *Sepia* | up to ~15% |
| *Chamomilla* | up to ~5% |
| *Calendula* | up to ~5% |

Methods of Use

As noted above, therapeutic patch embodiments may be placed over the naval cavity to seal the naval cavity area. In other embodiments, therapeutic patch embodiments may be placed elsewhere on the body. It has been found that placing the therapeutic patch over the naval cavity may provide some therapeutic advantage, however, other advantages may be found when patches are placed elsewhere on the body. As such, a therapeutic patch may be provided and applied to an area on the body including the naval cavity. Therapeutic patches may be removed upon relief of symptoms, upon relief of symptom causing activities, or upon expiration of a period of time such as for example up to 12 hours.

While this invention has been described in terms of several embodiments, there are alterations, permutations, and equivalents, which fall within the scope of this invention. It should also be noted that there are many alternative ways of implementing the methods and apparatuses of the present invention. Furthermore, unless explicitly stated, any method embodiments described herein are not constrained to a particular order or sequence. Further, the Abstract is provided herein for convenience and should not be employed to construe or limit the overall invention, which is expressed in the claims. It is therefore intended that the following appended claims be interpreted as including all such alterations, permutations, and equivalents as fall within the true spirit and scope of the present invention.

What is claimed is:

1. A therapeutic patch comprising:
a non-permeable sealing layer;
a pressure sensitive adhesive layer bonded along the non-permeable sealing layer, wherein
the pressure sensitive adhesive layer comprises a formulation of a pressure sensitive adhesive and a heat sensitive homeopathic formulation, wherein
the heat sensitive homeopathic formulation comprises a plurality of active ingredients selected for reducing nausea associated symptoms and menstrual cramping selected from the group consisting of:
*belladonna*, wherein the *belladonna* is present in approximately 5 to 30% by weight of the plurality of active ingredients,
magnesia phosphorica, wherein the magnesia phosphorica is present in approximately 5 to 30% by weight of the plurality of active ingredients,
colocynthis, wherein the colocynthis is present in approximately 5 to 30% by weight of the plurality of active ingredients,
*pulsatilla*, wherein the *pulsatilla* is present in approximately 1 to 10% by weight of the plurality of active ingredients
nux vomica, wherein the nux vomica is present in approximately 1 to 10% by weight of the plurality of active ingredients
*chamomilla*, wherein the *chamomilla* is present in approximately 1 to 5% by weight of the plurality of active ingredients, and
calendula, wherein the calendula is present in approximately 1 to 5% by weight of the plurality of active ingredients, wherein
the pressure sensitive adhesive layer is processed at a temperature less than approximately 100° F.; and
a releasable layer attached along the pressure sensitive adhesive layer.

2. The therapeutic patch of claim 1, wherein the therapeutic patch detectably reduces nausea associated symptoms and menstrual cramping.

3. The therapeutic patch of claim 1, wherein the pressure sensitive adhesive layer comprises at least approximately 15% by weight of the heat sensitive homeopathic formulation.

4. The therapeutic patch of claim 1, wherein the pressure sensitive adhesive layer comprises at least approximately 5 to 20% by weight of the heat sensitive homeopathic formulation.

5. The therapeutic patch of claim 1, wherein the pressure sensitive adhesive layer comprises at least approximately 2 to 30% by weight of the heat sensitive homeopathic formulation.

6. The therapeutic patch of claim 1, wherein the heat sensitive homeopathic formulation comprises:
a solvent.

7. The therapeutic patch of claim 6, wherein the solvent comprises approximately a 20% ethanol solution.

8. The therapeutic patch of claim 1, wherein the pressure sensitive adhesive is an acrylic copolymer.

9. The therapeutic patch of claim 1, wherein the non-permeable sealing layer is a polyethylene foam.

10. The therapeutic patch of claim 9, wherein the non-permeable sealing layer is a polyethylene foam is corona treated before bonding the pressure sensitive adhesive layer.

11. The therapeutic patch of claim 8, wherein the pressure sensitive adhesive has a peel value of approximately 1.5 pounds per square inch.

12. The therapeutic patch of claim 2, wherein the nausea associated symptoms are selected from the group consisting of: motion sickness, chemotherapy induced nausea vomiting (CINV), pregnancy (morning sickness), anxiety induced irritable bowel syndrome, Crohn's Disease, medication induced dizziness, vertigo, stress, migraines, general anxiety, and depression.

13. A therapeutic patch comprising:
a non-permeable sealing layer;
a pressure sensitive adhesive layer bonded along the non-permeable sealing layer, wherein
the pressure sensitive adhesive layer comprises a formulation of a pressure sensitive adhesive and a heat sensitive homeopathic formulation, wherein
the heat sensitive homeopathic formulation comprises a plurality of active ingredients selected for reducing nausea associated symptoms and menstrual cramping selected from the group consisting of:
*cocculus indicus*, wherein the *cocculus indicus* is present in approximately 5 to 20% by weight of the plurality of active ingredients,
nux vomica, wherein the nux vomica is present—in approximately 5 to 40% by weight of the plurality of active ingredients
*tabacum*, wherein the *tabacum* is present—in approximately 5 to 15% by weight of the plurality of active ingredients
sepia, wherein the sepia is present—in approximately 1 to 15% by weight of the plurality of active ingredients
*chamomilla*, wherein the *chamomilla* is present—in approximately 1 to 5% by weight of the plurality of active ingredients, and
calendula, wherein the calendula is present—in approximately 1 to 5% by weight of the plurality of active ingredients, wherein
the pressure sensitive adhesive layer is processed at a temperature less than approximately 100° F.; and
a releasable layer attached along the pressure sensitive adhesive layer.

14. The therapeutic patch of claim 13, wherein the pressure sensitive adhesive layer comprises at least approximately 15% by weight of the heat sensitive homeopathic formulation.

15. The therapeutic patch of claim 13, wherein the pressure sensitive adhesive layer comprises at least approximately 5 to 20% by weight of the heat sensitive homeopathic formulation.

16. The therapeutic patch of claim 13, wherein the pressure sensitive adhesive layer comprises at least approximately 2 to 30% by weight of the heat sensitive homeopathic formulation.

17. The therapeutic patch of claim 13, wherein the pressure sensitive adhesive is an acrylic copolymer.

18. The therapeutic patch of claim 13, wherein the non-permeable sealing layer is a polyethylene foam.

19. The therapeutic patch of claim 18, wherein the non-permeable sealing layer is a polyethylene foam is corona treated before bonding the pressure sensitive adhesive layer.

* * * * *